United States Patent [19]

Pallos et al.

[11] 4,124,372
[45] Nov. 7, 1978

[54] HERBICIDAL ANTIDOTE COMPOSITIONS WITH SUBSTITUTED OXAZOLIDINES AND THIAZOLIDINES

[75] Inventors: Ferenc M. Pallos, Walnut Creek, Calif.; Mervin E. Brokke, Stamford, Conn.; Duane R. Arneklev, Antelope, Mont.

[73] Assignee: Stauffer Chemical Company, Westport, Conn.

[21] Appl. No.: 710,503

[22] Filed: Aug. 2, 1976

Related U.S. Application Data

[60] Division of Ser. No. 356,547, May 2, 1973, Pat. No. 3,989,503, which is a continuation-in-part of Ser. No. 297,561, Oct. 13, 1972, abandoned, which is a continuation-in-part of Ser. No. 208,041, Dec. 9, 1971, abandoned, which is a continuation-in-part of Ser. No. 134,868, Apr. 16, 1971, abandoned.

[51] Int. Cl.² .................................................. A01N 9/22
[52] U.S. Cl. ........................................... 71/88; 71/90; 71/118
[58] Field of Search .............................. 71/88, 90, 118

[56] References Cited

U.S. PATENT DOCUMENTS

| | | | |
|---|---|---|---|
| 3,131,509 | 5/1964 | Hoffman | 71/100 |
| 3,719,466 | 3/1973 | Ahle | 71/100 |

*Primary Examiner*—Catherine L. Mills
*Attorney, Agent, or Firm*—Harry A. Pacini

[57] ABSTRACT

Herbicidal compositions comprising an active herbicidal compound and antidote therefor and the methods of use; the antidote compound corresponds to substituted oxazolidines and thiazolidines having the formula

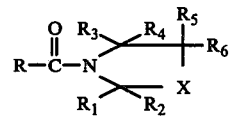

in which X is oxygen or sulfur; R is haloalkyl, alkyl or alkylthio; and $R_1$, $R_2$, $R_3$, $R_4$, $R_5$ and $R_6$ are independently selected from the group consisting of hydrogen, lower alkyl, alkoxyalkyl and lower alkylol.

109 Claims, No Drawings

HERBICIDAL ANTIDOTE COMPOSITIONS WITH SUBSTITUTED OXAZOLIDINES AND THIAZOLIDINES

CROSS REFERENCE TO RELATED APPLICATION

This is a division, of application Ser. No. 356,547 filed May 2, 1973 now U.S. Pat. No. 3,989,503 issued Nov. 2, 1976 which is a continuation-in-part of Ser. No. 297,561, filed Oct. 13, 1972, now abandoned which is a continuation-in-part of Ser. No. 208,041, filed Dec. 9, 1971 now abandoned which is a continuation-in-part of Ser. No. 134,868, filed Apr. 16, 1971, now abandoned.

BACKGROUND OF THE INVENTION

Among the many herbicidal compounds commercially available, the thiocarbamates alone or admixed with other herbicides, such as the triazines, have reached a relatively high degree of commercial success. These herbicides are immediately toxic to a large number of weed pests at different concentrations varying with the resistance of the weed pests. Some examples of these compounds are described and claimed in U.S. Pat. Nos. 2,913,327, 3,037,853, 3,175,897, 3,185,720, 3,198,786 and 3,582,314. It has been found in practice that the use of these thiocarbamates as herbicides on crops sometimes causes serious injuries to the crop plant. When used in the recommended amounts in the soil to control many broadleaf weeds and grasses, serious malformation and stunting of the crop plants result. This abnormal growth of the crop plants results in loss of crop yield. Previous attempts to overcome this problem involves the treatment of the crop seed with certain antagonistic agents prior to planting, see U.S. Pat. Nos. 3,131,509 and 3,564,768. These antagonistic agents have not been notably successful. The aforementioned patent specifically exemplifies the treatment of seeds employing compounds of a different chemical class not suggestive of the present invention.

Other preferred herbicidal compounds whose effect can be modified by the instant compounds include the acetanilides, such as 2-chloro-2',6'-diethyl-N-(methoxymethyl)acetanilide and the urea-type herbicides, such as 3-(3,4-dichlorophenyl)-1,1-dimethylurea.

DESCRIPTION OF THE INVENTION

It has been discovered that plants can be protected against injury by the thiolcarbamate-type herbicides, alone or mixed with other compounds and/or the tolerance of the plants can be substantially increased to the active compounds of the above-noted U.S. Patents by adding to the soil an antidote compound corresponding to the following formula:

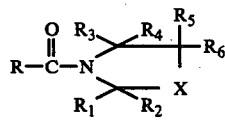

in which X is oxygen or sulfur; R is haloalkyl, alkyl or alkylthio; and $R_1$, $R_2$, $R_3$, $R_4$, $R_5$ and $R_6$ are independently selected from the group consisting of hydrogen, lower alkyl, alkoxyalkyl and lower alkylol.

In the above description, the following embodiments are intended for the various substituent groups: for R, haloalkyl and alkyl preferably includes, unless otherwise provided for, those members which contain from 1 to 10 carbon atoms, inclusive, in both straight chain and branched chain configurations, and the term halo includes chloro and bromo as mono, di, tri, tetra and per substitutions. As exemplary of the alkyl portion within the preferred embodiment are the following: methyl, ethyl, n-propyl, isopropyl, n-butyl, sec.-butyl, 1,1-dimethylbutyl, amyl, isoamyl, 2,4,4-trimethylpentyl, n-hexyl, isohexyl, n-heptyl, n-octyl, isooctyl, nonyl, and decyl. The term alkylthio preferably includes those members which contain from 1 to 4 carbon atoms, inclusive, for example, methylthio, ethylthio, n-propylthio, isopropylthio, n-butylthio, t-butylthio, and the like. For $R_1$, $R_2$, $R_3$, $R_4$, $R_5$ and $R_6$, the term lower alkyl preferably includes, unless otherwise provided for, those members which contain from 1 to 4 carbon atoms, inclusive, for example, methyl, ethyl, n-propyl, isopropyl, n-butyl, sec.-butyl, tert.-butyl, and the like. The term alkoxyalkyl preferably includes those members having a total of 2 to 4 carbon atoms, inclusive for example, methoxymethyl, methoxyethyl, ethoxyethyl, ethoxymethyl and the like. The term lower alkylol preferably includes those members having 1 to 4 carbon atoms, inclusive for example, methylol, ethylol, propylol and butylol.

As an alternative mode of action, the compounds of this invention may interfere with the normal herbicidal action of the thiocarbamate-type and other herbicides to render them selective in their action. Whichever mode of action is present, the corresponding beneficial and desirable effect is the continued herbicidal effect of the thiocarbamate with the accompanying decreased herbicidal effect on desired crop species. This advantage and utility will become more apparent hereinafter.

Therefore, the terms herbicide, antidote or anitdotal amount, is meant to describe that effect which tends to counteract the normal injurious herbicidal response that the herbicide might otherwise produce. Whether it is to be termed a remedy, interferant, protectant, or the like, will depend upon the exact mode of action. The mode of action is varied, but the effect, which is desirable, is the result of the method of treating the soil in which a crop is planted. Hitherto, there have been no systems which have been satisfactory for this purpose.

The compounds of this invention represented by the above formula can be prepared by several different procedures depending upon the starting materials.

The oxazolidine and thiazolidine intermediates were prepared by the condensation of the amino alcohol or mercaptan with a suitable aldehyde or ketone in boiling benzene with the continuous separation of water. This method is described by Bergmann et al., JACS 75 358 (1953). Usually, the oxazolidines and thiazolidines intermediates were pure enough to be used directly without further purification. Aliquots of these solutions were then used to prepare the compounds of this invention.

The appropriate intermediate was reacted with an acid chloride in the presence of a hydrogen chloride acceptor, such as triethylamine, to prepare the desired compound. Workup and purification procedures involved standard methods of extration, distillation or crystallization.

The compounds of the present invention and their preparation are more particularly illustrated by the following examples. Following the examples of preparation is a table of compounds which are prepared according to the procedures described herein. Compound numbers have been assigned to them and are used for

EXAMPLE IA

Preparation of 2,2-dimethyl-3-dichloroacetyl oxazolidine

Five and one-tenth (5.1g.) grams of 2,2-dimethyl oxazolidine dissolved in 50 ml. of benzene was treated with 5.5 g. of triethylamine and 7.4 g. of dichloroacetyl chloride was added dropwise with stirring and cooling in an ice bath. The mixture was poured into water, the benzene solution separated, dried over anhydrous magnesium sulfate and the solvent stripped under vacuum. The product was a waxy solid which had a melting point of 113°–115° C. on recrystallization from diethyl ether.

EXAMPLE IB

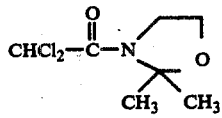

15 g. of acetone and 12.2 g. of ethanol amine were combined in 150 ml. of benzene and refluxed until no additional water came over. The resulting solution was examined and found to contain 2,2-dimethyl-1,3-oxazolidine. A quarter of the benzene solution (0.05 mole) was reacted with 7.4 g. of dichloroacetyl chloride and 5.5 g. of triethylamine, washed with water, dried and stripped under vacuum to give a light tan solid. A portion was recrystallized from ether giving a white product.

EXAMPLE II

Preparation of 2,2,5-trimethyl-3-dichloroacetyl oxazolidine

Eighteen (18) milliliters of a benzene solution containing 4.6 g. of 2,2,5-trimethyl oxazolidine was added to 25 ml. of benzene and 4.5 g. of triethylamine. Five and nine-tenths (5.9 g.) grams of dichloroacetyl chloride was added dropwise with stirring and cooling in an ice bath. When reaction was complete the mixture was poured into water and the benzene layer separated, dried over anhydrous magnesium sulfate and the benzene removed under vacuum. Yield was 7.7 g. of an oil, $n_D^{30} = 1.4950$.

EXAMPLE III

Preparation of 2,2-dimethyl-3-dichloroacetyl thiazolidine

Four and seven-tenths (4.7 g.) grams of 2,2-dimethyl thiazolidine and 4.5 g. of triethylamine were dissolved in 50 ml. of methylene chloride and 5.9 g. of dichloroacetyl chloride was added dropwise with stirring. The mixture was cooled in a water bath at room temperature. When reaction was complete, the mixture was poured into water and the solvent layer separated, dried over anhydrous magnesium sulfate, and the solvent removed under vacuum. Yield was 3.6 g. of a waxy solid. Recrystallization of another sample from diethyl ether gave a white solid, m.p. 109°–111° C.

EXAMPLE IV

Preparation of 2,2,5-trimethyl-3(2,′,3′-dibromopropionyl)oxazolidine

Fourteen (14 ml.) milliliters of a benzene solution containing 3.5 g. of 2,2,5-trimethyl oxazolidine was added to 25 ml. of benzene and 3.5 g. of triethylamine. Seven and one-half (7.5 g.) grams of 2,3-dibromopropionyl chloride was added dropwise with stirring and cooling in an ice bath. When reaction was complete, the mixture was poured into water and benzene layer separated, dried over anhydrous magnesium sulfate and the solvent stripped under vacuum. The yield was 5.7 g. of an oil, $n_D^{30} = 1.5060$.

EXAMPLE V

Preparation of 2,2-dimethyl-3-dibromoacetyl thiazolidine

To a mixture of 3.5 g. of 2,2-dimethyl thiazolidine, 50 ml. of benzene and 7.1 g. of dibromoacetyl chloride mixed in an ice bath was added 3.1 g. of triethylamine dropwise with stirring and continued cooling. When reaction was complete, the mixture was poured into water and the benzene layer separated, dried over magnesium sulfate and the benzene removed under vacuum. Yield was 8.5 g. of a dark oil.

EXAMPLE VI

Preparation of 2-ethyl-3-S-ethylthiocarbonyl oxazolidine

Sixteen and one half (16.5 ml.) milliliters of a benzene solution of 2-ethyl oxazolidine was added to 50 ml. of benzene and 4.1 g. of triethylamine. Five (5 g.) grams of ethyl chlorothiolformate was added dropwise with stirring and cooling in an ice bath. The mixture was poured into water and the benzene solution separated, dried over anhydrous magnesium sulfate and the benzene stripped under vacuum. Yield was 5.6 g. of an oil, $n_D^{30} = 1.5130$.

EXAMPLE VII

Preparation of 2,2-dimethyl-3-heptanoyl oxazolidine

Sixteen and one-half (16.5 ml.) milliliters of a benzene solution containing 4.6 g. of 2,2-dimethyl oxazolidine was added to 50 ml. of benzene and 4.1 g. of triethylamine. To this mixture 6 g. of n-heptanoyl chloride was added dropwise with stirring and cooling in an ice bath. The mixture was poured into water and the benzene layer extracted, dried over magnesium sulfate and the benzene removed under vacuum. Yield was 7.5 g. of an oil, $n_D^{30} = 1.4598$.

TABLE I

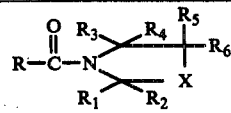

| COMPOUND NUMBER | R | $R_1$ | $R_2$ | $R_3$ | $R_4$ | $R_5$ | $R_6$ | X | m.p. °C. or $n_D^{30}$ |
|---|---|---|---|---|---|---|---|---|---|
| 1 | $CHCl_2$ | $CH_3$ | $CH_3$ | H | H | H | H | O | 116–118 |

TABLE I-continued $$\underset{R_1}{\overset{R_3}{\underset{R_2}{R-C-N}}}\overset{R_5}{\underset{X}{\overset{R_4}{-}}}\overset{}{\underset{R_6}{}}$$

Structure: R-C(=O)-N(R3)-C(R1)(R2)-C(R4)(R5)(R6), with X on the second carbon

| COMPOUND NUMBER | R | $R_1$ | $R_2$ | $R_3$ | $R_4$ | $R_5$ | $R_6$ | X | m.p. °C. or $n_D^{30}$ |
|---|---|---|---|---|---|---|---|---|---|
| 2 | $CH_2Cl$ | $CH_3$ | $CH_3$ | H | H | H | H | O | 1.4932 |
| 3 | $CBr_3$ | $CH_3$ | $CH_3$ | H | H | H | H | O | 1.5560 |
| 4 | $CBr_3$ | $CH_3$ | $CH_3$ | H | H | $CH_3$ | H | O | Glass |
| 5 | $CH_2Cl$ | $CH_3$ | $CH_3$ | H | H | $CH_3$ | H | O | 1.4842 |
| 6 | $CHCl_2$ | $CH_3$ | $CH_3$ | H | H | $CH_3$ | H | O | 1.4950 |
| 7 | $CH_2Cl$ | $CH_3$ | $CH_3$ | $C_2H_5$ | H | H | H | O | 1.4900 |
| 8 | $CHCl_2$ | $CH_3$ | $CH_3$ | $C_2H_5$ | H | H | H | O | 1.4950 |
| 9 | $CCl_3$ | $CH_3$ | $CH_3$ | $C_2H_5$ | H | H | H | O | 1.4970 |
| 10 | $CBr_3$ | $CH_3$ | $CH_3$ | $C_2H_5$ | H | H | H | O | 1.5428 |
| 11 | $CH_3CHBr$ | $CH_3$ | $CH_3$ | H | H | $CH_3$ | H | O | 1.4993 |
| 12 | $CH_3CHBr$ | $CH_3$ | $CH_3$ | $C_2H_5$ | H | H | H | O | 1.4993 |
| 13 | $CH_2Cl$ | $CH_3$ | $C_2H_5$ | H | H | H | H | O | 1.4928 |
| 14 | $CHCl_2$ | $CH_3$ | $C_2H_5$ | H | H | H | H | O | 1.4982 |
| 15 | $CCl_3$ | $CH_3$ | $C_2H_5$ | H | H | H | H | O | 1.5034 |
| 16 | $CH_3CHBr$ | $CH_3$ | $C_2H_5$ | H | H | H | H | O | 1.5058 |
| 17 | $CBr_3$ | $CH_3$ | $C_2H_5$ | H | H | H | H | O | 95-97 |
| 18 | $CH_2Br$ | $CH_3$ | $C_2H_5$ | H | H | H | H | O | 1.5097 |
| 19 | $CH_2Br$ | $CH_3$ | $CH_3$ | H | H | $CH_3$ | H | O | 1.5020 |
| 20 | $CH_2Br$ | $CH_3$ | $CH_3$ | $C_2H_5$ | H | H | H | O | 1.5048 |
| 21 | $CH_3(CHBr)_4$ | $CH_3$ | $CH_3$ | H | H | H | H | O | 1.5658 |
| 22 | $CH_2Cl$ | $CH_3$ | $CH_3$ | $CH_3$ | $CH_3$ | H | H | O | 1.4843 |
| 23 | $CHCl_2$ | $CH_3$ | $CH_3$ | $CH_3$ | $CH_3$ | H | H | O | 120-123 |
| 24 | $CCl_3$ | $CH_3$ | $CH_3$ | $CH_3$ | $CH_3$ | H | H | O | 1.5031 |
| 25 | $CH_2Br$ | $CH_3$ | $CH_3$ | $CH_3$ | $CH_3$ | H | H | O | 1.5116 |
| 26 | $CH_3CHBr$ | $CH_3$ | $CH_3$ | $CH_3$ | $CH_3$ | H | H | O | 1.5140 |
| 27 | $CBr_3$ | $CH_3$ | $CH_3$ | $CH_3$ | $CH_3$ | H | H | O | 1.5610 |
| 28 | $ClCH_2CH_2$ | $CH_3$ | $CH_3$ | H | H | H | H | O | 1.4538 |
| 29 | $CHCl_2$ | $C_2H_5$ | H | H | H | H | H | S | 1.5458 |
| 30 | $CHCl_2$ | $CH_3$ | $CH_3$ | H | H | H | H | S | 109-111 |
| 31 | $CH_2BrCHBr$ | $CH_3$ | $C_2H_5$ | H | H | H | H | O | 1.5170 |
| 32 | $CH_2BrCHBr$ | $CH_3$ | $CH_3$ | H | H | $CH_3$ | H | O | 1.5060 |
| 33 | $CH_2BrCHBr$ | $CH_3$ | $CH_3$ | $C_2H_5$ | H | H | H | O | 1.5083 |
| 34 | $CH_2BrCHBr$ | $CH_3$ | $CH_3$ | H | H | H | H | O | 1.5178 |
| 35 | $CH_2BrCHBr$ | $CH_3$ | $t-C_4H_9$ | H | H | H | H | O | 1.5165 |
| 36 | $CHCl_2$ | $CH_3$ | $t-C_4H_9$ | H | H | H | H | O | 1.4949 |
| 37 | $CBr_3$ | $CH_3$ | $t-C_4H_9$ | H | H | H | H | O | 1.5431 |
| 38 | $CHCl_2$ | H | H | $CH_3$ | $CH_3$ | H | H | O | 1.5033 |
| 39 | $CHCl_2$ | $CH_3OCH_2$ | H | H | H | H | H | O | 1.5132 |
| 40 | $CHCl_2$ | $C_3H_7$ | H | H | H | H | H | O | 1.4988 |
| 41 | $CHCl_2$ | $C_2H_5$ | H | H | H | H | H | O | 1.5126 |
| 42 | $CHBr_2$ | $C_2H_5$ | H | H | H | H | H | O | 1.5750 |
| 43 | $CBr_3$ | $C_2H_5$ | H | H | H | H | H | O | 1.5610 |
| 44 | $CH_2Br$ | $C_2H_5$ | H | H | H | H | H | O | 1.5200 |
| 45 | $CH_3CHBr$ | $C_2H_5$ | H | H | H | H | H | O | 1.5140 |
| 46 | $(CH_3)_2CBr$ | $C_2H_5$ | H | H | H | H | H | O | 1.4958 |
| 47 | $CH_2BrCHBr$ | $C_2H_5$ | H | H | H | H | H | O | 1.5273 |
| 48 | $CH_2Cl$ | $C_2H_5$ | H | H | H | H | H | O | 1.5020 |
| 49 | $CHCl_2$ | $C_2H_5$ | H | H | H | $CH_3$ | H | O | 1.4955 |
| 50 | $CH_2Cl$ | $C_2H_5$ | H | H | H | $CH_3$ | H | O | 1.4890 |
| 51 | $CH_2Br$ | $C_2H_5$ | H | H | H | $CH_3$ | H | O | 1.5064 |
| 52 | $CHBr_2$ | $C_2H_5$ | H | H | H | $CH_3$ | H | O | Glass |
| 53 | $CBr_3$ | $C_2H_5$ | H | H | H | $CH_3$ | H | O | Glass |
| 54 | $CH_3CHBr$ | $C_2H_5$ | H | H | H | $CH_3$ | H | O | 1.4978 |
| 55 | $CH_2BrCHBr$ | $C_2H_5$ | H | H | H | $CH_3$ | H | O | 1.5138 |
| 56 | $(CH_3)_2CBr$ | $C_2H_5$ | H | H | H | $CH_3$ | H | O | 1.4851 |
| 57 | $CHCl_2$ | H | H | $C_2H_5$ | H | H | H | O | 1.5030 |
| 58 | $CHBr_2$ | H | H | $C_2H_5$ | H | H | H | O | Dark liquid |
| 59 | $CBr_3$ | H | H | $C_2H_5$ | H | H | H | O | 1.5531 |
| 60 | $CH_2Br$ | H | H | $C_2H_5$ | H | H | H | O | 1.5173 |
| 61 | $CH_3CHBr$ | H | H | $C_2H_5$ | H | H | H | O | 1.5076 |
| 62 | $(CH_3)_2CBr$ | H | H | $C_2H_5$ | H | H | H | O | 1.4852 |
| 63 | $CH_2BrCHBr$ | H | H | $C_2H_5$ | H | H | H | O | 1.5249 |
| 64 | $CCl_3$ | H | H | $C_2H_5$ | H | H | H | O | 1.5048 |
| 65 | $CH_2Cl$ | H | H | $C_2H_5$ | H | H | H | O | 1.4998 |
| 66 | $CHCl_2$ | $CH_3$ | H | H | H | H | H | O | 1.5112 |
| 67 | $CCl_3$ | $CH_3$ | H | H | H | H | H | O | 1.5148 |
| 68 | $CH_2Cl$ | $CH_3$ | H | H | H | H | H | O | 1.5077 |
| 69 | $CH_2Br$ | $CH_3$ | H | H | H | H | H | O | 1.5263 |
| 70 | $CHBr_2$ | $CH_3$ | H | H | H | H | H | O | 1.5471 |
| 71 | $CBr_3$ | $CH_3$ | H | H | H | H | H | O | Dark liquid |
| 72 | $CH_2BrCHBr$ | $CH_3$ | H | H | H | H | H | O | 1.5280 |
| 73 | $CH_3CHBr$ | $CH_3$ | H | H | H | H | H | O | 1.5162 |
| 74 | $(CH_3)_2CBr$ | $CH_3$ | H | H | H | H | H | O | 1.5013 |
| 75 | $CHCl_2$ | $CH_3$ | H | H | H | $CH_3$ | H | O | 1.4983 |
| 76 | $CCl_3$ | $CH_3$ | H | H | H | $CH_3$ | H | O | 1.4990 |
| 77 | $CH_2Cl$ | $CH_3$ | H | H | H | $CH_3$ | H | O | 1.4958 |
| 78 | $CHBr_2$ | $CH_3$ | H | H | H | $CH_3$ | H | O | Dark liquid |
| 79 | $CH_3CHBr$ | $CH_3$ | H | H | H | $CH_3$ | H | O | 1.5083 |
| 80 | $CHBr_2$ | $C_2H_5$ | H | H | H | H | H | S | 1.5782 |
| 81 | $CH_2BrCHBr$ | $C_2H_5$ | H | H | H | H | H | S | 1.5650 |
| 82 | $CCl_3$ | $CH_3$ | $CH_3$ | H | H | H | H | S | 1.5638 |
| 83 | $CHBr_2$ | $CH_3$ | $CH_3$ | H | H | H | H | S | Dark liquid |
| 84 | $CH_3CHBr$ | $CH_3$ | $CH_3$ | H | H | H | H | S | 1.5520 |
| 85 | $CHCl_2$ | H | H | H | H | H | H | S | 75-77 |
| 86 | $CHCl_2$ | $CH_3$ | $i-C_3H_7$ | H | H | H | H | O | 1.4960 |
| 87 | $CHCl_2$ | $CH_3$ | $CH_3$ | $CH_3$ | $CH_2OH$ | H | H | O | 1.4960 |

TABLE I-continued

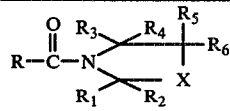

| COMPOUND NUMBER | R | $R_1$ | $R_2$ | $R_3$ | $R_4$ | $R_5$ | $R_6$ | X | m.p. °C. or $n_D^{30}$ |
|---|---|---|---|---|---|---|---|---|---|
| 88 | $CH_2BrC(CH_3)Br$ | $C_2H_5$ | H | H | H | H | H | O | 1.5318 |
| 89 | $CH_2BrC(CH_3)Br$ | $C_2H_5$ | H | H | H | $CH_3$ | H | O | 1.5225 |
| 90 | $CH_2BrC(CH_3)Br$ | $CH_3$ | H | H | H | $CH_3$ | H | O | 1.5210 |
| 91 | $CHCl_2$ | $C_2H_5$ | H | $C_2H_5$ | H | H | H | O | 1.4947 |
| 92 | $C_2H_5S$ | H | H | $C_2H_5$ | H | H | H | O | 1.4998 |
| 93 | $C_2H_5S$ | $CH_3$ | H | H | H | $CH_3$ | H | O | 1.4965 |
| 94 | $C_2H_5S$ | $C_2H_5$ | H | H | H | $CH_3$ | H | O | 1.4973 |
| 95 | $C_2H_5S$ | $C_2H_5$ | H | $C_2H_5$ | H | H | H | O | 1.4928 |
| 96 | $CCl_3$ | $C_2H_5$ | H | $C_2H_5$ | H | H | H | O | 1.4937 |
| 97 | $CH_2BrCHBr$ | $C_2H_5$ | H | $C_2H_5$ | H | H | H | O | 1.5198 |
| 98 | $CH_2BrC(CH_3)Br$ | $C_2H_5$ | H | $C_2H_5$ | H | H | H | O | 1.5202 |
| 99 | $CH_2BrCH_2$ | $C_2H_5$ | H | $C_2H_5$ | H | H | H | O | 1.4920 |
| 100 | $CHCl_2$ | $CH_3$ | H | $C_2H_5$ | H | H | H | O | 1.4960 |
| 101 | $C_3H_7S$ | $CH_3$ | H | $C_2H_5$ | H | H | H | O | 1.4900 |
| 102 | $i$-$C_3H_7S$ | $CH_3$ | H | $C_2H_5$ | H | H | H | O | 1.4875 |
| 103 | $CCl_3$ | $CH_3$ | H | $C_2H_5$ | H | H | H | O | 1.4990 |
| 104 | $CH_2Br$ | $CH_3$ | H | $C_2H_5$ | H | H | H | O | 1.5070 |
| 105 | $CH_2BrCHBr$ | $CH_3$ | H | $C_2H_5$ | H | H | H | O | 1.5168 |
| 106 | $CH_2BrC(CH_3)Br$ | $CH_3$ | H | $C_2H_5$ | H | H | H | O | 1.5160 |
| 107 | $CH_2BrCH_2$ | $CH_3$ | H | $C_2H_5$ | H | H | H | O | 1.4950 |
| 108 | $C_4H_9S$ | $CH_3$ | H | $C_2H_5$ | H | H | H | O | 1.4928 |
| 109 | $C_4H_9S$ | $C_2H_5$ | H | $C_2H_5$ | H | H | H | O | 1.4880 |
| 110 | $CH_3S$ | $CH_3$ | H | $C_2H_5$ | H | H | H | O | 1.4980 |
| 111 | $C_6H_{13}$ | $CH_3$ | $CH_3$ | H | H | H | H | O | 1.4598 |
| 112 | $CH_3S$ | $CH_3$ | $CH_3$ | $C_2H_5$ | H | H | H | O | 1.4913 |
| 113 | $n$-$C_3H_7S$ | $CH_3$ | $CH_3$ | $C_2H_5$ | H | H | H | O | 1.4858 |
| 114 | $i$-$C_3H_7S$ | $CH_3$ | $CH_3$ | $C_2H_5$ | H | H | H | O | 1.4828 |
| 115 | $CH_2BrCH_2$ | $CH_3$ | $CH_3$ | H | H | H | H | O | 1.4912 |
| 116 | $CH_2BrCHBr$ | H | H | $CH_3$ | $CH_3$ | H | H | O | 1.5221 |
| 117 | $CH_2BrCH_2$ | $CH_3$ | $CH_3$ | H | H | H | H | S | 1.5263 |
| 118 | $CH_2BrCHBr$ | $CH_3$ | $CH_3$ | H | H | H | H | S | 1.5573 |
| 119 | $CH_2BrCH_2$ | H | H | $CH_3$ | $CH_3$ | H | H | O | 1.4890 |
| 120 | $CH_2Br$ | H | H | H | H | H | H | S | 1.6032 |
| 121 | $CH_3CHBr$ | H | H | H | H | H | H | S | 1.5720 |
| 122 | $CH_2BrCH_2$ | H | H | H | H | H | H | S | 1.5629 |
| 123 | $CH_2BrCHBr$ | H | H | H | H | H | H | S | 1.5742 |
| 124 | $CH_3C(CH_3)Br$ | H | H | H | H | H | H | S | 1.5420 |
| 125 | $CH_2ClCH_2$ | H | H | H | H | H | H | S | 1.5475 |
| 126 | $BrCH_2(CH_2)_8CH_2$ | $CH_3$ | $CH_3$ | H | H | H | H | O | 1.4898 |
| 127 | $ClCH_2CH_2CH_2$ | $CH_3$ | $CH_3$ | H | H | H | H | O | 1.4880 |
| 128 | $ClCH_2CH_2CH_2$ | $CH_3$ | $CH_3$ | H | H | H | H | S | 1.5183 |
| 129 | $CH_3CHClCH_2$ | $CH_3$ | $CH_3$ | H | H | H | H | O | 1.4896 |
| 130 | $CH_3CHClCH_2$ | $CH_3$ | $CH_3$ | H | H | H | H | O | 1.5115 |
| 131 | $CH_3CHClCH_2$ | $CH_3$ | $CH_3$ | H | H | $CH_3$ | H | O | 1.4701 |
| 132 | $C_2H_5CHBr$ | $CH_3$ | $CH_3$ | H | H | H | H | O | 1.5020 |
| 133 | $C_2H_5CHBr$ | $CH_3$ | $CH_3$ | H | H | H | H | S | 1.5288 |
| 134 | $C_2H_5CHBr$ | $CH_3$ | $CH_3$ | H | H | $CH_3$ | H | O | 1.4900 |
| 135 | $C_3H_7CHBr$ | $CH_3$ | $CH_3$ | H | H | H | H | O | 1.4972 |
| 136 | $C_3H_7CHBr$ | $CH_3$ | $CH_3$ | H | H | H | H | S | 1.5220 |
| 137 | $C_3H_7CHBr$ | $CH_3$ | $CH_3$ | H | H | $CH_3$ | H | O | 1.4870 |
| 138 | $CH_2ClCH_2CH_2$ | $CH_3$ | $CH_3$ | H | H | $CH_3$ | H | O | 1.4747 |
| 139 | $CH_2Br(CH_2)_4$ | $CH_3$ | $CH_3$ | H | H | H | H | O | 1.4970 |
| 140 | $CH_2Br(CH_2)_4$ | $CH_3$ | $CH_3$ | H | H | $CH_3$ | H | O | 1.4886 |
| 141 | $CH_2Br(CH_2)_4$ | $CH_3$ | $CH_3$ | H | H | H | H | S | 1.5249 |
| 142 | $CHCl_2$ | H | H | H | H | H | H | O | 1.5136 |
| 143 | $CH_2BrCBr(CH_3)$ | H | H | H | H | H | H | S | Semi-solid |
| 144 | $CH_2Cl$ | H | H | H | H | H | H | S | 1.5540 |
| 145 | $CHCl_2$ | $CH_3$ | $C_2H_5$ | H | H | H | H | S | 1.5443 |
| 146 | $CH_3CHBr$ | $CH_3$ | $C_2H_5$ | H | H | H | H | S | 1.4327 |
| 147 | $CH_2BrCH_2$ | $CH_3$ | $C_2H_5$ | H | H | H | H | S | 1.4293 |
| 148 | $CH_2Cl$ | $CH_3$ | $C_2H_5$ | H | H | H | H | S | 1.5279 |

The compounds of this invention were employed in effective herbicidal antidote compositions comprising thiocarbamates in combination with antidote compounds described hereinabove. They were tested in the following manner.

CORN SEED TREATMENT TEST

Small flats were filled with Felton loamy sand soil. Soil incorporated herbicides were applied at this time. The soil from each flat was placed into a five-gallon cement mixer where the soil was mixed as the herbicides were applied using a predetermined amount of a stock solution containing 936 mg. of 75.5% active ingredient to 100 ml. of water. One ml. of stock solution was applied to the soil in a volumetric pipet for each pound of herbicide desired. One ml. of stock solution contained 7 mg. of herbicide which equals one pound per acre when applied to the soil in the flats. After the herbicide incorporation, the soil was placed back into the flats.

Flats of herbicide-treated and untreated soil were then ready to be planted. A pint sample of soil was removed from each flat and placed next to each flat for later use in covering up the seeds. The soil was leveled and rows one-half inch deep were made for planting seeds. Alternating rows of treated and untreated crop seeds were sown. In each test, six PAG 344T field corn seeds were planted in each row. Rows were approximately 1-½ inches apart in the flat. Seed were treated by either (1) placing 50 mg. of the antidote compound with 10 grams of corn seed (0.5% w/w) in a suitable container and shaking them until the seeds were uniformly covered with the compound, or (2) preparing a stock solution by dissolving 50 mg. of the antidote compound in 5 ml. of acetone, then using 0.5 ml. of the stock solution to treat 10 g. of corn seed (0.05% w/w). Antidote compounds were also applied as liquid slurries and powders or dusts. In some cases, acetone was used to dissolve powdered or solid compounds so they could be more effectively applied to the seeds.

After the flats were seeded, they were covered with the one pint of soil which had been removed just prior to planting. Flats were placed on greenhouse benches where temperatures ranged from 70°–90° F. Flats were watered by sprinkling as needed to assure good plant growth. Per cent control ratings were taken two, three and four weeks after the treatments were applied.

In each test, the herbicide was applied alone, in combination with the seed protectant, and the seed protectant was applied alone to check for phytotoxicity. The untreated adjacent row was employed to observe any beneficial lateral movement of the antidote compound through the soil. The degree of the effect was noted by comparison with the control. The results of these tests are tabulated in Table II.

TABLE II

Per Cent Injury to Corn from EPTC*
Seed Treatment Test

| COMPOUND NUMBER | Per Cent Injury, 2 weeks | |
|---|---|---|
| | Treated Seed (0.05% w/w) | Untreated Seed Adjacent Row |
| 1 | 0 | 0 |
| 1** | 5 | 30 |
| 2 | 70 | 80 |
| 3** | 40 | 60 |
| 4 | 10 | 50 |
| 5 | 30 | 60 |
| 6 | 0 | 0 |
| 7 | 40 | 55 |
| 8 | 0 | 15 |
| 9 | 10 | 55 |
| 10 | 20 | 60 |
| 11 | 30 | 50 |
| 12 | 10 | 40 |
| 13 | 50 | 70 |
| 14 | 0 | 20 |
| 15 | 20 | 50 |
| 16 | 10 | 55 |
| 17 | 30 | 50 |
| 18 | 20 | 50 |
| 19 | 40 | 50 |
| 20 | 20 | 60 |
| 21 | 50 | 50 |
| 22 | 60 | 60 |
| 23 | 50 | 60 |
| 24 | 20 | 60 |
| 25 | 20 | 70 |
| 26 | 20 | 60 |
| 27 | 20 | 60 |
| 28 | 60 | 70 |
| 29 | 0 | 5 |
| 30 | 20 | 5 |
| 142*** | 10 | 75 |
| EPTC 6E Untreated Seed | — | 70 |
| | | 80 (4 weeks) |

* = S-ethyl dipropylthiocarbamate 6E: 6 lb/A preplant incorporated
** = Seed treatment 0.01% w/w
*** = Seed treatment 0.5% w/w With 2-chloro-2',6'-diethyl-N-methoxymethyl)acetanilide at 2 lb/A as a seed treatment, 0.5%, Compound No. 145 gave 100% protection to sorghum (Milo).

PROCEDURE: MULTICROP ANTIDOTE SCREEN

Plastic flats were filled with Felton loamy sand soil. Since a variety of grass and broadleaf crops were used in these tests, EPTAM ® (EPTC) was incorporated at ½ and 5 lb/A, while a constant rate of 5 lb/A of the additive was used. EPTAM ® (EPTC) and the herbicide additive were applied separately by pipetting measured amounts of the appropriate stock solutions into the soil during incorporation in a 5 gallon rotary cement mixer. Stock solutions for EPTAM were prepared as follows:

A. ½ lb/A: 670 mg. of EPTC 6E (75.5% a.i.) was diluted with 500 ml. of deionized water so that 2 ml. equals ½ lb/A/plastic flat.
B. 5 lb/A: 6700 mg. of EPTC 6E (75.5%) was diluted with 500 ml. of deionized water so that 2 ml. equals 5 lb/A/plastic flat.

Additive stock solutions were prepared by diluting 102 mg. of technical material with 10 ml. of acetone 1% Tween 20 ® (polyoxyethylene sorbitan monolaurate) so that 2 ml. equals 5 lb/A/flat.

After the soil was treated with both herbicide and additive, the soil was transferred from the mixer back into the flat where it was then prepared for seeding. The initial step in preparation was to remove a one pint sample of soil from each flat to be retained and used to cover the seeds after planting. The soil was then leveled and rows one-quarter inch deep were made in each flat. Flats treated with 5 lb/A of EPTAM were seeded to DeKalb XL-44 corn (*Zea maize*), US H9 sugarbeets (*Beta vulgare*), small seeded gray striped sunflower (*Helianthus annus*), Acala cotton (*Gossypium hirsutum*), Brag soybeans (*Glycine max*) and oilseed rape (*Brassica napus*), Flats treated with ½ lb/A of EPTAM were seeded to red oats (*Avena byzantina*), R-10 milo [sorghum] (*Sorghum vulgare*), Fremont HRS wheat (*Triticum aestivum*), giant foxtail (*Seteria feberii*), Calrose rice (*Oryza sativa*) and Blue Mariate barley (*Hordeum vulgare*). Seeds were then covered with the pint soil sample removed prior to seeding.

The flats were then placed on greenhouse benches where temperatures were maintained between 70°–90° F. The soil was watered by sprinkling to assure good plant growth.

Injury ratings were taken 2 and 4 weeks after the treatments were applied. Soil treated with EPTAM alone at ½ or 5 lb/A was included to provide a basis for determining the amount of injury reduction provided by the herbicide antidotes. The percent protection of various representative crops is reported in Table III. The per cent protection is determined by a comparison with flats not treated with the candidate antidote.

TABLE III

| COMPOUND NUMBER | Multicrop Screen Results Per Cent Protection | | % Protection (2 weeks) |
|---|---|---|---|
| | Rate of EPTC lb/A | Crop | |
| 31 | 0.5 | barley | 56 |
| | | rice | 30 |
| 32 | 0.5 | barley | 56 |
| | | rice | 30 |
| | 5.0 | corn | 100 |
| 33 | 0.5 | rice | 30 |
| | | barley | 44 |
| 34 | 0.5 | barley | 88 |
| | 5.0 | corn | 100 |
| 35 | 0.5 | barley | 44 |
| | 5.0 | corn | 100 |
| 36 | 5.0 | corn | 100 |
| 37 | 5.0 | corn | 100 |
| 38 | 0.5 | barley | 88 |
| | 5.0 | corn | 100 |
| | 5.0 | sunflower | 50 |
| 39 | 5.0 | corn | 100 |
| | 5.0 | sunflower | 25 |
| | 5.0 | oilseed rape | 60 |
| 40 | 5.0 | corn | 100 |
| | 5.0 | sunflower | 25 |

TABLE III-continued

Multicrop Screen Results Per Cent Protection

| COMPOUND NUMBER | Rate of EPTC lb/A | Crop | % Protection (2 weeks) | |
|---|---|---|---|---|
| 41 | 0.5 | barley | 50 | |
|  | 5.0 | corn | 100 | (4 weeks) |
| 42 | 5.0 | corn | 56 | (4 weeks) |
| 43 | 5.0 | corn | 93 | (4 weeks) |
| 44 | 5.0 | corn | 28 | (4 weeks) |
| 45 | 0.5 | barley | 50 | |
|  | 5.0 | sunflower | 81 | |
| 46 | 0.5 | rice | 100 | (4 weeks) |
| 47 | 0.5 | rice | 100 | (4 weeks) |
|  | 0.5 | barley | 75 | (4 weeks) |
|  | 5.0 | oilseed rape | 68 | (4 weeks) |
| 48 | 0.5 | barley | 25 | |
|  | 5.0 | sunflower | 67 | (4 weeks) |
| 49 | 0.5 | sorghum | 50 | |
|  | 0.5 | barley | 50 | |
|  | 5.0 | corn | 100 | (4 weeks) |
| 50 | 5.0 | corn | 100 | (4 weeks) |
| 51 | 5.0 | corn | 42 | (4 weeks) |
| 52 | 5.0 | corn | 100 | (4 weeks) |
| 53 | 0.5 | rice | 100 | (4 weeks) |
|  | 0.5 | barley | 50 | (4 weeks) |
|  | 5.0 | corn | 70 | (4 weeks) |
| 54 | 0.5 | barley | 50 | |
|  | 5.0 | corn | 100 | (4 weeks) |
| 55 | 0.5 | wheat | 20 | (4 weeks) |
|  | 0.5 | barley | 100 | (4 weeks) |
|  | 5.0 | corn | 93 | (4 weeks) |
| 56 | 0.5 | sorghum | 10 | (4 weeks) |
| 57 | 0.5 | barley | 50 | |
|  | 5.0 | corn | 100 | (4 weeks) |
| 58 | 0.5 | rice | 100 | (4 weeks) |
| 59 | 5.0 | corn | 93 | (4 weeks) |
| 60 | 0.5 | rice | 100 | (4 weeks) |
|  | 5.0 | corn | 42 | (4 weeks) |
| 61 | 0.5 | sorghum | 40 | (4 weeks) |
|  | 0.5 | barley | 75 | (4 weeks) |
|  | 5.0 | rice | 70 | (4 weeks) |
| 62 | 5.0 | oilseed rape | 65 | (4 weeks) |
| 63 | 0.5 | barley | 75 | |
| 64 | 5.0 | corn | 42 | (4 weeks) |
| 65 | 5.0 | corn | 70 | (4 weeks) |
| 66 | 5.0 | corn | 100 | (4 weeks) |
| 67 | 5.0 | corn | 28 | (4 weeks) |
| 68 | 0.5 | rice | 100 | (4 weeks) |
|  | 5.0 | corn | 93 | (4 weeks) |
| 69 | 5.0 | corn | 42 | (4 weeks) |
| 70 | 5.0 | corn | 100 | (4 weeks) |
| 71 | 5.0 | corn | 70 | (4 weeks) |
| 72 | 0.5 | rice | 100 | (4 weeks) |
|  | 0.5 | barley | 50 | (4 weeks) |
|  | 5.0 | corn | 100 | (4 weeks) |
| 73 | 5.0 | corn | 100 | (4 weeks) |
| 74 | 5.0 | corn | 42 | (4 weeks) |
| 75 | 0.5 | sorghum | 71 | |
|  | 0.5 | wheat | 60 | |
|  | 5.0 | corn | 87 | |
|  | 5.0 | oilseed rape | 71 | |
| 76 | 5.0 | corn | 56 | (4 weeks) |
| 77 | 5.0 | corn | 100 | (4 weeks) |
|  | 5.0 | sugarbeets | 28 | (4 weeks) |
| 78 | 0.5 | rice | 100 | (4 weeks) |
|  | 5.0 | corn | 100 | (4 weeks) |
|  | 5.0 | sunflower | 81 | (4 weeks) |
| 79 | 0.5 | barley | 50 | |
|  | 5.0 | corn | 100 | (4 weeks) |
|  | 5.0 | sunflower | 67 | (4 weeks) |
| 80 | 5.0 | corn | 70 | (4 weeks) |
|  | 5.0 | oilseed rape | 56 | (4 weeks) |
| 81 | 0.5 | barley | 50 | (4 weeks) |
|  | 5.0 | sunflower | 67 | (4 weeks) |
| 82 | 5.0 | corn | 56 | (4 weeks) |
| 83 | 0.5 | rice | 100 | (4 weeks) |
| 84 | 0.5 | rice | 100 | (4 weeks) |
|  | 0.5 | barley | 50 | (4 weeks) |
| 85 | 0.5 | rice | 100 | (4 weeks) |
|  | 0.5 | barley | 75 | (4 weeks) |
|  | 5.0 | corn | 93 | (4 weeks) |
| 86 | 0.5 | barley | 50 | (4 weeks) |
|  | 5.0 | corn | 100 | (4 weeks) |
| 87 | 5.0 | corn | 93 | (4 weeks) |
| 88 | 0.5 | barley | 45 | |
| 89 | 0.5 | wheat | 67 | |
|  | 5.0 | oilseed rape | 75 | |
| 90 | 0.5 | wheat | 15 | |
| 91 | 0.5 | sorghum | 50 | |
|  | 5.0 | corn | 84 | |
| 92 | 5.0 | oilseed rape | 75 | |
| 93 | 5.0 | oilseed rape | 75 | |
| 94 | 5.0 | oilseed rape | 75 | |
| 95 | 5.0 | oilseed rape | 75 | |
| 96 | 5.0 | corn | 80 | |
| 97 | 0.5 | barley | 50 | |
| 98 | 5.0 | sunflower | 60 | |
| 99 | 0.5 | barley | 88 | |
| 100 | 5.0 | corn | 100 | |
| 101 | 5.0 | sunflower | 100 | |
| 102 | 5.0 | oilseed rape | 50 | |
| 103 | 0.5 | sorghum | 30 | (4 weeks) |
|  | 5.0 | corn | 100 | |
| 104 | 0.5 | rice | 30 | (4 weeks) |
|  | 0.5 | sorghum | 30 | (4 weeks) |
| 105 | 0.5 | wheat | 30 | (4 weeks) |
|  | 0.5 | barley | 75 | (4 weeks) |
| 106 | 5.0 | sunflower | 20 | (4 weeks) |
| 107 | 0.5 | wheat | 40 | (4 weeks) |
|  | 0.5 | barley | 60 | (4 weeks) |
|  | 5.0 | corn | 100 | (4 weeks) |
| 108 | 5.0 | oilseed rape | 75 | |
| 109 | 5.0 | oilseed rape | 75 | |
| 110 | 5.0 | oilseed rape | 75 | |
| 111 | 5.0 | sunflower | 60 | |
| 112 | 5.0 | oilseed rape | 75 | |
| 113 | 5.0 | oilseed rape | 67 | |
| 114 | 5.0 | oilseed rape | 33 | |
| 115 | 0.5 | barley | 70 | (4 weeks) |
|  | 5.0 | corn | 10 | (4 weeks) |
| 116 | 0.5 | barley | 58 | (4 weeks) |
|  | 5.0 | sunflower | 60 | (4 weeks) |
|  | 5.0 | corn | 100 | (4 weeks) |
| 117 | 0.5 | barley | 58 | (4 weeks) |
|  | 5.0 | corn | 100 | (4 weeks) |
| 118 | 0.5 | barley | 58 | (4 weeks) |
|  | 5.0 | corn | 65 | (4 weeks) |
| 119 | 0.5 | barley | 68 | (4 weeks) |
|  | 5.0 | corn | 100 | (4 weeks) |
| 120 | 5.0 | sunflower | 30 | |
| 121 | 0.5 | rice | 67 | (4 weeks) |
|  | 5.0 | oilseed rape | 60 | (4 weeks) |
| 122 | 0.5 | barley | 58 | (4 weeks) |
|  | 5.0 | corn | 100 | (4 weeks) |
| 123 | 0.5 | rice | 44 | (4 weeks) |
| 124 | 0.5 | rice | 67 | (4 weeks) |
|  | 0.5 | barley | 58 | (4 weeks) |
| 125 | 0.5 | rice | 88 | (4 weeks) |
| 126 | 0.5 | rice | 100 | |
|  | 0.5 | barley | 100 | |
| 127 | 0.5 | rice | 78 | |
|  | 0.5 | barley | 64 | |
| 128 | 0.5 | rice | 78 | |
|  | 0.5 | barley | 57 | |
|  | 5.0 | oilseed rape | 60 | |
| 129 | 0.5 | rice | 78 | |
|  | 0.5 | barley | 43 | |
|  | 5.0 | sunflower | 100 | |
| 130 | 0.5 | rice | 100 | |
|  | 0.5 | barley | 43 | |
|  | 5.0 | oilseed rape | 40 | |
|  | 5.0 | soybeans | 33 | |
| 131 | 0.5 | barley | 43 | |
|  | 5.0 | sunflower | 100 | |
|  | 5.0 | oilseed rape | 80 | |
|  | 5.0 | soybeans | 47 | |
| 132 | 0.5 | rice | 78 | |
|  | 0.5 | oats | 50 | |
|  | 0.5 | barley | 57 | |
|  | 5.0 | oilseed rape | 100 | |
|  | 5.0 | corn | 58 | |
| 133 | 0.5 | barley | 57 | |
|  | 0.5 | oats | 40 | |
|  | 5.0 | sugarbeets | 45 | |
|  | 5.0 | oilseed rape | 100 | |
| 134 | 0.5 | barley | 43 | |
|  | 5.0 | soybeans | 33 | |
|  | 5.0 | oilseed rape | 80 | |
| 135 | 0.5 | oats | 60 | |
|  | 5.0 | corn | 100 | |
|  | 5.0 | oilseed rape | 100 | |
| 136 | 0.5 | rice | 55 | |
|  | 0.5 | barley | 57 | |
|  | 5.0 | corn | 100 | |
|  | 5.0 | oilseed rape | 80 | |
| 137 | 0.5 | barley | 43 | |
|  | 0.5 | sunflower | 70 | |
|  | 5.0 | soybeans | 33 | |
| 138 | 0.5 | rice | 78 | |
|  | 0.5 | barley | 71 | |
|  | 5.0 | oilseed rape | 60 | |
| 139 | 5.0 | sunflower | 70 | |

TABLE III-continued

| COMPOUND NUMBER | Multicrop Screen Results Per Cent Protection | | |
|---|---|---|---|
| | Rate of EPTC lb/A | Crop | % Protection (2 weeks) |
| | 5.0 | oilseed rape | 60 |
| 140 | 5.0 | sunflower | 100 |
| | 5.0 | oilseed rape | 60 |
| | 5.0 | soybeans | 33 |
| 141 | 5.0 | soybeans | 47 |
| | 5.0 | oilseed rape | 60 |
| 142 | 0.5 | rice | 86 |
| | 0.5 | barley | 62.5 |
| 143 | 0.5 | rice | 100 |
| | 0.5 | barley | 87.5 |
| 144 | 0.5 | sorghum | 100 |
| | 0.5 | rice | 86 |
| | 0.5 | barley | 100 |
| | 5.0 | corn | 100 |
| 145 | 0.5 | rice | 100 |
| | 0.5 | barley | 100 |
| 146 | 0.5 | barley | 75 |
| | 5.0 | oilseed rape | 100 |
| 147 | 0.5 | rice | 72 |
| | 5.0 | corn | 88 |

When used with 2-chloro-2',6'-diethyl-N-(methoxymethyl) acetanilide at 2 lb/A, Compounds No. 1 and 30 at 5 lb/A after 4 weeks gave 100 percent protection to sorghum. Compoun No. 1 also gave 67 percent protection to wheat.

When used with 3-(3,4-dichlorophenyl)-1,1-dimethylurea at 1 lb/A, Compounds No. 1 and 30 at 5 lb/A each gave 60 percent protection to cotton; Compound No. 1 also gave 60 percent protection to corn; and Compound No. 30 gave 43 percent protection to corn.

The antidote compounds and compositions of the present invention can be used in any convenient form. Thus, the antidote compounds can be formulated into emulsifiable liquids, emulsifiable concentrates, liquid, wettable powder, powders, granular or any other convenient form. In its preferred form, a non-phytotoxic quantity of an herbicidal antidote compound is admixed with a selected herbicide and incorporated into the soil prior to or after planting the seed. It is to be understood, however, that the herbicides can be incorporated into the soil and thereafter the antidote compound can be incorporated into the soil. Moreover, the crop seed itself can be treated with a non-phytotoxic quantity of the compound and planted into the soil which has been treated with herbicides, or untreated with the herbicide and subsequently treated with the herbicide. The addition of the antidote compound does not affect the herbicidal activity of the herbicides.

The amount of antidote compound present can range between about 0.0001 to about 30 parts by weight of antidote compound described herein per each part by weight of herbicide. The exact amount of antidote compound will usually be determined on economic ratios for the most effective amount usable. It is understood that a non-phytotoxic quantity of antidote compound will be employed in the herbicidal compositions described herein.

The herbicides indicated in the tables and elsewhere are used at rates which produce effective control of undesirable vegetation. The range of rates employed herein produce representative results within the recommended amounts set forth by the supplier. Therefore, the weed control in each instance is commercially acceptable within the desired or recommended amount.

It is clear that the classes of herbicidal agents described and illustrated herein are characterized as effective herbicides exhibiting such activity. The degree of this herbicidal activity varies among specific compounds and among combinations of specific compounds within the classes. Similarly, the degree of activity to some extent varies among the species of plants to which a specific herbicidal compound or combination may be applied. Thus, selection of a specific herbicidal compound or combination to control undesirable plant species readily may be made. Within the present invention are prevention of injury to a desired crop species in the presence of a specific compound or combination may be achieved. The beneficial plant species which can be protected by this method is not intended to be limited by the specific crops employed in the examples.

The herbicidal compounds employed in the utility of this invention are active herbicides of a general type. That is, the members of the classes are herbicidally effective against a wide range of plant species with no discrimination between desirable and undesirable species. The method of controlling vegetation comprises applying an herbicidally effective amount of the hereindescribed herbicidal compounds to the area or plant locus where control is desired. The compositions as set forth in this invention include those wherein the preferred active herbicidal compound is selected from EPTC, S-ethyl diisobutyl thiocarbamate, S-propyl dipropyl thiocarbamate, S-2,3,3-trichloroallyl-diisopropyl thiocarbamate, S-ethyl cyclohexyl ethyl thiocarbamate, 2-chloro-2',6'-diethyl-N-(methoxymethyl)acetanilide, S-ethyl hexahydro-1H-azepine-1-carbothioate, 2-chloro-N-isopropylacetanilide, N,N-diallyl-2-chloroacetamide, S-4-chlorobenzyl diethyl thiocarbamate, 2-chloro-4-ethylamino-6-isopropylamino-s-triazine, 2-chloro-4,6-bis(ethylamino)-s-triazine, 2(4-chloro-6-ethylamine-s-triazine-2-yl-amino)-2-methylpropionitrile, 2-chloro-4-cyclopropylamino-6-isopropylamino-s-triazine, 2,4-dichlorophenoxyacetic acid, its esters and salts, and 3-(3,4-dichlorophenyl)-1,1-dimethylurea and combinations thereof.

An herbicide as used herein means a compound which controls or modifies the growth of vegetation or plants. Such controlling or modifying effects include all deviations from natural development; for example, killing, retardation, defoliation, desiccation, regulation, stunting, tillering, stimulation, dwarfing and the like. By "plants", it is meant germinant seeds, emerging seedlings, and established vegetation, including the roots and above-ground portions.

What is claimed is:

1. An herbicidal composition comprising an active α-halo substituted acetanilide herbicide compound and an antidote therefor corresponding to the formula

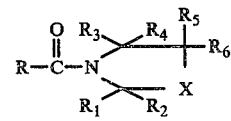

in which X is oxygen or sulfur, R is haloalkyl having 1 to 10 carbon atoms, inclusive, and the term halo includes chloro and bromo substitutions, alkyl having 1 to 10 carbon atoms, inclusive, or alkylthio having 1 to 4 carbon atoms, inclusive; $R_1$, $R_2$, $R_3$, $R_4$, $R_5$ and $R_6$ are independently selected from the group consisting of hydrogen, lower alkyl having 1 to 4 carbon atoms, inclusive, alkoxyalkyl having a total of 2 to 4 carbon atoms, inclusive, and lower alkylol having 1 to 4 carbon atoms, inclusive; said antidote being antidotally active with said α-halo substituted acetanilide herbicide compound.

2. The composition as set forth in claim 1 wherein X is oxygen, R is haloalkyl, $R_1$ is lower alkyl, $R_2$ is lower alkyl and $R_3$, $R_4$, $R_5$ and $R_6$ are each hydrogen.

3. A composition according to claim 2 in which R is dichloromethyl, $R_1$ is methyl and $R_2$ is methyl.

4. A composition according to claim 2 in which R is monochloromethyl, $R_1$ is methyl and $R_2$ is methyl.

5. A composition according to claim 2 in which R is tribromomethyl, $R_1$ is methyl and $R_2$ is methyl.

6. A composition according to claim 2 in which R is monochloromethyl, $R_1$ is methyl and $R_2$ is ethyl.

7. A composition according to claim 2 in which R is dichloromethyl, $R_1$ is methyl and $R_2$ is ethyl.

8. A composition according to claim 2 in which R is trichloromethyl, $R_1$ is methyl and $R_2$ is ethyl.

9. A composition according to claim 2 in which R is 1-bromoethyl, $R_1$ is methyl and $R_2$ is ethyl.

10. A composition according to claim 2 in which R is tribromomethyl, $R_1$ is methyl and $R_2$ is ethyl.

11. A composition according to claim 2 in which R is monobromomethyl, $R_1$ is methyl and $R_2$ is ethyl.

12. A composition according to claim 2 in which R is 1,2,4,4-tetrabromopentyl, $R_1$ is methyl and $R_2$ is methyl.

13. A composition according to claim 2 in which R is 2-chloroethyl, $R_1$ is methyl and $R_2$ is methyl.

14. A composition according to claim 2 in which R is 1,2-dibromoethyl, $R_1$ is methyl and $R_2$ is ethyl.

15. A composition according to claim 2 in which R is 1,2-dibromoethyl, $R_1$ is methyl and $R_2$ is methyl.

16. A composition according to claim 2 in which R is 1,2-dibromoethyl, $R_1$ is methyl and $R_2$ is t-butyl.

17. A composition according to claim 2 in which R is dichloromethyl, $R_1$ is methyl and $R_2$ is t-butyl.

18. A composition according to claim 2 in which R is tribromomethyl, $R_1$ is methyl and $R_2$ is t-butyl.

19. A composition according to claim 2 in which R is dichloromethyl, $R_1$ is methyl and $R_2$ is i-propyl.

20. A composition according to claim 2 in which R is 2-bromoethyl, $R_1$ is methyl and $R_2$ is methyl.

21. A composition according to claim 2 in which R is ω-bromodecyl, $R_1$ is methyl and $R_2$ is methyl.

22. A composition according to claim 2 in which R is 3-chloropropyl, $R_1$ is methyl and $R_2$ is methyl.

23. A composition according to claim 2 in which R is 2-chloropropyl, $R_1$ is methyl and $R_2$ is methyl.

24. A composition according to claim 2 in which R is 1-bromopropyl, $R_1$ is methyl and $R_2$ is methyl.

25. A composition according to claim 2 in which R is 1-bromobutyl, $R_1$ is methyl and $R_2$ is methyl.

26. A composition according to claim 2 in which R is 5-bromopentyl, $R_1$ is methyl and $R_2$ is methyl.

27. A composition according to claim 1 wherein X is oxygen, R is alkyl, $R_1$ is lower alkyl, $R_2$ is lower alkyl and $R_3$, $R_4$, $R_5$ and $R_6$ are each hydrogen.

28. A composition according to claim 27 in which R is hexyl, $R_1$ is methyl and $R_2$ is methyl.

29. The composition as set forth in claim 1 wherein X is sulfur, R is haloalkyl, $R_1$ is lower alkyl, $R_2$ is lower alkyl and $R_3$, $R_4$, $R_5$ and $R_6$ are each hydrogen.

30. A composition according to claim 29 in which R is dichloromethyl, $R_1$ is methyl and $R_2$ is methyl.

31. A composition according to claim 29 in which R is trichloromethyl, $R_1$ is methyl and $R_2$ is methyl.

32. A composition according to claim 29 in which R is dibromomethyl, $R_1$ is methyl and $R_2$ is methyl.

33. A composition according to claim 29 in which R is 1-bromoethyl, $R_1$ is methyl and $R_2$ is methyl.

34. A composition according to claim 29 in which R is 2-bromoethyl, $R_1$ is methyl and $R_2$ is methyl.

35. A composition according to claim 29 in which R is 1,2,-dibromoethyl, $R_1$ is methyl and $R_2$ is methyl.

36. A composition according to claim 29 in which R is 3-chloropropyl, $R_1$ is methyl and $R_2$ is methyl.

37. A composition according to claim 29 in which R is 2-chloropropyl, $R_1$ is methyl and $R_2$ is methyl.

38. A composition according to claim 29 in which R is i-bromopropyl, $R_1$ is methyl and $R_2$ is methyl.

39. A composition according to claim 29 in which R is 1-bromobutyl, $R_1$ is methyl and $R_2$ is methyl.

40. A composition according to claim 29 in which R is 5-bromopentyl, $R_1$ is methyl and $R_2$ is methyl.

41. A composition according to claim 29 in which R is dichloromethyl, $R_1$ is methyl and $R_2$ is ethyl.

42. A composition according to claim 29 in which R is 1-bromoethyl, $R_1$ is methyl and $R_2$ is ethyl.

43. A composition according to claim 29 in which R is 2-bromoethyl, $R_1$ is methyl and $R_2$ is ethyl.

44. A composition according to claim 29 in which R is monochloromethyl, $R_1$ is methyl and $R_2$ is ethyl.

45. The composition as set forth in claim 1 wherein X is oxygen, R is haloalkyl, $R_1$ is lower alkyl, $R_2$ is lower alkyl, $R_5$ is lower alkyl and $R_3$, $R_4$, and $R_6$ are each hydrogen.

46. A composition according to claim 45 in which R is tribromomethyl, $R_1$ is methyl, $R_2$ is methyl and $R_5$ is methyl.

47. A composition according to claim 45 in which R is monchloromethyl, $R_1$ is methyl, $R_2$ is methyl and $R_5$ is methyl.

48. A composition according to claim 45 in which R is dichloromethyl, $R_1$ is methyl, $R_2$ is methyl and $R_5$ is methyl.

49. A composition according to claim 45 in which R is 1-bromoethyl, $R_1$ is methyl, $R_2$ is methyl and $R_5$ is methyl.

50. A composition according to claim 45 in which R is monobromoethyl, $R_1$ is methyl, $R_2$ is methyl and $R_5$ is methyl.

51. A composition according to claim 45 in which R is 1,2-dibromoethyl, $R_1$ is methyl, $R_2$ is methyl and $R_5$ is methyl.

52. A composition according to claim 45 in which R is 2-chloropropyl, $R_1$ is methyl, $R_2$ is methyl and $R_5$ is methyl.

53. A composition according to claim 45 in which R is 1-bromopropyl, $R_1$ is methyl, $R_2$ is methyl and $R_5$ is methyl.

54. A composition according to claim 45 in which R is 1-bromobutyl, $R_1$ is methyl, $R_2$ is methyl and $R_5$ is methyl.

55. A composition according to claim 45 in which R is 3-chloropropyl, $R_1$ is methyl, $R_2$ is methyl and $R_5$ is methyl.

56. A composition according to claim 45 in which R is 6-bromopentyl, $R_1$ is methyl, $R_2$ is methyl and $R_5$ is methyl.

57. The composition as set forth in claim 1 wherein X is oxygen, R is haloalkyl, $R_1$ is lower alkyl, $R_2$ is lower alkyl, $R_3$ is lower alkyl, $R_4$, $R_5$ and $R_6$ are each hydrogen.

58. The composition as set forth in claim 1 wherein X is oxygen, R is haloalkyl, $R_1$ is lower alkyl, $R_2$ is lower alkyl, R₃ is lower alkyl and R₄ is lower alkyl, R₅ and R₆ are each hydrogen.

59. The composition as set forth in claim 1 wherein X is oxygen, R is haloalkyl, R₁, R₂, R₃, R₄ and R₅ are each independently lower alkyl and R₆ is hydrogen.

60. The composition as set forth in claim 1 wherein X is oxygen, R is haloalkyl, R₁ is alkoxyalkyl, R₂, R₃, R₄, R₅ and R₆ are each hydrogen.

61. The composition according to claim 60 in which R is dichloromethyl and R₁ is methoxymethyl.

62. The composition as set forth in claim 1 wherein X is oxygen, R is haloalkyl, R₁ is lower alkyl, R₅ is lower alkyl and R₂, R₃, R₄ and R₆ are each hydrogen.

63. The composition as set forth in claim 1 wherein X is oxygen, R is haloalkyl, R₃ is lower alkyl and R₁, R₂, R₄, R₅ and R₆ are each hydrogen.

64. The composition as set forth in claim 1 in which X is oxygen, R is dichloromethyl, R₁, R₂, R₃, R₄, R₅ and R₆ are each hydrogen.

65. The composition as set forth in claim 1 in which X is sulfur, R is dichloromethyl, R₁ is ethyl, R₂, R₃, R₄, R₅ and R₆ are each hydrogen.

66. The method of protecting a grass crop from injury due to a α-halo substituted acetanilide herbicide, comprising applying to the grass crop seed prior to planting a non-phytotoxic antidotally effective amount of a compound corresponding to the formula

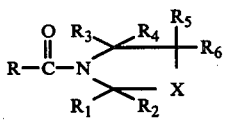

in which X is oxygen or sulfur, R is haloalkyl having 1 to 10 carbon atoms, inclusive, and the term halo includes chloro and bromo substitutions, alkyl having 1 to 10 carbon atoms, inclusive, or alkylthio having 1 to 4 carbon atoms, inclusive; R₁, R₂, R₃, R₄, R₅ and R₆ are independently selected from the group consisting of hydrogen, lower alkyl having 1 to 4 carbon atoms, inclusive, alkoxyalkyl having a total of 2 to 4 carbon atoms, inclusive, and lower alkylol having 1 to 4 carbon atoms, inclusive; said antidote being antidotally active with said α-halo substituted acetanilide herbicide compound on said crop.

67. In the method according to claim 66 in which said substituted acetanilide herbicide is 2-chloro-2′,6′-diethyl-N-(methoxymethyl) acetanilide and the antidote compound has the formula wherein R is dichloromethyl, R₁ is methyl, R₂ is methyl and R₃, R₄, R₅ and R₆ are each hydrogen.

68. The method of protecting a grass crop from injury due to a α-halo substituted acetanilide herbicide, comprising preplant incorporation in the soil in which said grass crop is to be planted, a non-phytotoxic antidotally effective amount of a compound corresponding to the formula

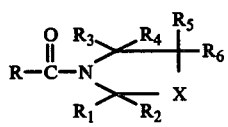

in which X is oxygen or sulfur, R is haloalkyl having 1 to 10 carbon atoms, inclusive, and the term halo includes chloro and bromo substitutions, alkyl having 1 to 10 carbon atoms, inclusive, or alkylthio having 1 to 4 carbon atoms, inclusive; R₁, R₂, R₃, R₄, R₅ and R₆ are independently selected from the group consisting of hydrogen, lower alkyl having 1 to 4 carbon atoms, inclusive, alkoxyalkyl having a total of 2 to 4 carbon atoms, inclusive, and lower alkylol having 1 to 4 carbon atoms, inclusive, said antidote being antidotally active with said α-halo substituted acetanilide herbicide compound on said grass crop.

69. The herbicidal composition as set forth in claim 1 wherein said active substituted acetanilide is selected from the group consisting of 2-chloro-2′6′-diethyl-N-(methoxymethyl) acetanilide, and 2-chloro-N-isopropyl acetanilide.

70. The herbicidal composition as set forth in claim 45 wherein an active acetanilide is selected from the group consisting of 2-chloro-2′6′-diethyl-N-(methyoxymethyl) acetanilide and 2-chloro-N-isopropyl acetanilide.

71. The herbicidal composition according to claim 70 in which R is monochloromethyl, R₁ is methyl, R₂ is methyl and R₅ is methyl.

72. The herbicidal composition according to claim 70 in which R is dichloromethyl, R₁ is methyl, R₂ is methyl and R₅ is methyl.

73. The herbicidal composition according to claim 69 wherein X is oxygen, R is haloalkyl, R₁ is lower alkyl, R₂ is lower alkyl, R₃ is lower alkyl, and R₄, R₅ and R₆ are each hydrogen.

74. The herbicidal composition as set forth in claim 69 wherein X is oxygen, R is haloalkyl, R₁ is lower alkyl, R₂ is lower alkyl, R₃ is lower alkyl, R₄ is lower alkyl, and R₅ and R₆ are each hydrogen.

75. The herbicidal composition as set forth in claim 69 wherein X is oxygen, R is haloalkyl, R₁, R₂, R₃, R₄ and R₅ are each independently lower alkyl, and R₆ is hydrogen.

76. The herbicidal composition as set forth in claim 69 wherein X is oxygen, R is haloalkyl, R₁ is alkoxyalkyl, and R₂, R₃, R₄, R₅ and R₆ are each hydrogen.

77. The herbicidal composition as set forth in claim 69 wherein X is oxygen, R is haloalkyl, R₁ is lower alkyl, R₅ is lower alkyl, and R₂, R₃, R₄ and R₆ are each hydrogen.

78. The herbicidal composition as set forth in claim 69 wherein X is oxygen, R is haloalkyl, R₃ is lower alkyl, and R₁, R₂, R₄, R₅ and R₆ are each hydrogen.

79. The method according to claim 66 in which X is oxygen, R is haloalkyl, R₁ is lower alkyl, R₂ is lower alkyl, R₅ is lower alkyl, and R₃, R₄ and R₆ are each hydrogen.

80. A composition according to claim 79 in which R is dichloromethyl, R₁ is methyl, R₂ is methyl, and R₅ is methyl.

81. The method according to claim 66 in which X is oxygen, R is haloalkyl, R₁ is lower alkyl, R₂ is lower alkyl, R₃ is lower alkyl, and R₄, R₅ and R₆ are each hydrogen.

82. The method according to claim 66 in which X is oxygen, R is haloalkyl, R₁ is lower alkyl, R₂ is lower alkyl, R₃ is lower alkyl, R₄ is lower alkyl, and R₅ and R₆ are each hydrogen.

83. The method according to claim 66 in which X is oxygen, R is haloalkyl, R₁, R₂, R₃, R₄ and R₅ are each independently lower alkyl and R₆ is hydrogen.

84. The method according to claim 66 in which X is oxygen, R is haloalkyl, R₁ is alkoxyalkyl, and R₂, R₃, R₄, R₅ and R₆ are each hydrogen.

85. The method according to claim 66 in which X is oxygen, R is haloalkyl, $R_1$ is lower alkyl, $R_5$ is lower alkyl, and $R_2$, $R_3$, $R_4$ and $R_6$ are each hydrogen.

86. The method according to claim 66 in which X is oxygen, R is haloalkyl, $R_3$ is lower alkyl, and $R_1$, $R_2$, $R_4$, $R_5$ and $R_6$ are each hydrogen.

87. The method of protecting a grass plant crop from injury due to an active α-halo substituted acetanilide herbicidal compound, comprising applying to the soil in which an herbicidally effective amount of said α-halo substituted acetanilide herbicide compound is used, a non-phytotoxic antidotally effective amount of a compound corresponding to the formula

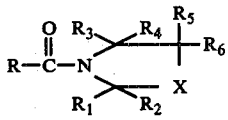

in which X is oxygen or sulfur, R is haloalkyl having 1 to 10 carbon atoms, inclusive, and the term halo includes chloro and bromo substitutions, alkyl having 1 to 10 carbon atoms, inclusive, or alkylthio having 1 to 4 carbon atoms, inclusive; $R_1$, $R_2$, $R_3$, $R_4$, $R_5$ and $R_6$ are independently selected from the group consisting of hydrogen, lower alkyl having 1 to 4 carbon atoms, inclusive, alkoxyalkyl having a total of 2 to 4 carbon atoms, inclusive, and lower alkylol having 1 to 4 carbon atoms, inclusive; said antidote being antidotally active with said α-halo substituted acetanilide herbicide compound on said grass crop.

88. The method according to claim 87, in which X is oxygen, R is haloalkyl, $R_1$ is lower alkyl, $R_2$ is lower alkyl, $R_5$ is lower alkyl, and $R_3$, $R_4$, and $R_6$ are each hydrogen.

89. The method according to claim 88 in which R is dichloromethyl, $R_1$ is methyl, $R_2$ is methyl, and $R_5$ is methyl.

90. The method according to claim 87 in which X is oxygen, R is haloalkyl, $R_1$ is lower alkyl, $R_2$ is lower alkyl, $R_3$ is lower alkyl, and $R_4$, $R_5$ and $R_6$ are each hydrogen.

91. The method according to claim 87 in which X is oxygen, R is haloalkyl, $R_1$ is lower alkyl, $R_2$ is lower alkyl, $R_3$ is lower alkyl, $R_4$ is lower alkyl, and $R_5$ and $R_6$ are each hydrogen.

92. The method according to claim 87 in which X is oxygen, R is haloalkyl, $R_1$, $R_2$, $R_3$, $R_4$ and $R_5$ are each independently lower alkyl, and $R_6$ is hydrogen.

93. The method according to claim 87 in which X is oxygen, R is haloalkyl, $R_1$ is alkoxyalkyl, and $R_2$, $R_3$, $R_4$, $R_5$ and $R_6$ are each hydrogen.

94. The method according to claim 87 in which X is oxygen, R is haloalkyl, $R_1$ is lower alkyl, $R_5$ is lower alkyl, and $R_2$, $R_3$, $R_4$ and $R_6$ are each hydrogen.

95. The method according to claim 87 in which X is oxygen, R is haloalkyl, $R_3$ is lower alkyl, and $R_1$, $R_2$, $R_4$, $R_5$ and $R_6$ are each hydrogen.

96. The method of protecting a grass plant crop from injury due to a herbicidally active α-halo substituted acetanilide compound comprising applying to the soil a herbicidal composition, comprising a herbicidally effective amount of an active α-halo substituted acetanilide and an antidotally effective amount of an antidote compound having the formula

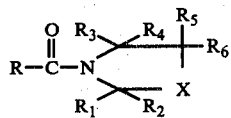

in which X is oxygen or sulfur, R is haloalkyl having 1 to 10 carbon atoms, inclusive, and the term halo includes chloro and bromo substitutions, alkyl having 1 to 10 carbon atoms, inclusive, or alkylthio having 1 to 4 carbon atoms, inclusive; $R_1$, $R_2$, $R_3$, $R_4$, $R_5$ and $R_6$ are independently selected from the group consisting of hydrogen, lower alkyl having 1 to 4 carbon atoms, inclusive, alkoxyalkyl having a total of 2 to 4 carbon atoms, inclusive, and lower alkylol having 1 to 4 carbon atoms, inclusive; said antidote being antidotally active with said α-halo substituted acetanilide herbicide compound on said grass crop.

97. The method according to claim 96 in which X is oxygen, R is haloalkyl, $R_1$ is lower alkyl, $R_2$ is lower alkyl, $R_5$ is lower alkyl, and $R_3$, $R_4$ and $R_6$ are each hydrogen.

98. The method according to claim 97 in which R is dichloromethyl, $R_1$ is methyl, $R_2$ is methyl, and $R_5$ is methyl.

99. The method according to claim 96 in which X is oxygen, R is haloalkyl, $R_1$ is lower alkyl, $R_2$ is lower alkyl, $R_3$ is lower alkyl, and $R_4$, $R_5$ and $R_6$ are each hydrogen.

100. The method according to claim 96 in which X is oxygen, R is haloalkyl, $R_1$ is lower alkyl, $R_2$ is lower alkyl, $R_3$ is lower alkyl, $R_4$ is lower alkyl, and $R_5$ and $R_6$ are each hydrogen.

101. The method according to claim 96 in which X is oxygen, R is haloalkyl, $R_1$, $R_2$, $R_3$, $R_4$ and $R_5$ are each independently lower alkyl, and $R_6$ is hydrogen.

102. The method according to claim 96 in which X is oxygen, R is haloalkyl, $R_1$ is alkoxyalkyl, and $R_2$, $R_3$, $R_4$, $R_5$ and $R_6$ are each hydrogen.

103. The method according to claim 96 in which X is oxygen, R is haloalkyl, $R_1$ is lower alkyl, $R_5$ is lower alkyl, and $R_2$, $R_3$, $R_4$ and $R_6$ are each hydrogen.

104. The method according to claim 96 in which X is oxygen, R is haloalkyl, $R_3$ is lower alkyl, and $R_1$, $R_2$, $R_4$, $R_5$ and $R_6$ are each hydrogen.

105. An herbicidal composition according to claim 1 in which the α-halo substituted acetanilide is α-chloro substituted acetanilide.

106. The method of claim 66 in which α-halo substituted acetanilide is α-chloro substituted acetanilide.

107. The method of claim 68 in whith α-halo substituted acetanilide is α-chloro substituted acetanilide.

108. The method of claim 87 in which α-halo substituted acetanilide is α-chloro substituted acetanilide.

109. The method of claim 96 in which α-halo substituted acetanilide is α-chloro substituted acetanilide.

* * * * *